United States Patent [19]

Kroll

[11] Patent Number: 4,832,608

[45] Date of Patent: May 23, 1989

[54] ELECTRODE BELT ADAPTER

[75] Inventor: Mark W. Kroll, Minnetonka, Minn.

[73] Assignee: Cherne Medical, Inc., Minneapolis, Minn.

[21] Appl. No.: 53,313

[22] Filed: May 22, 1987

[51] Int. Cl.$^4$ ............................................. H01R 9/09
[52] U.S. Cl. ..................................... 439/67; 128/641; 439/465
[58] Field of Search ............................. 439/67, 74–77, 439/82, 467, 491–493, 488, 329–331, 473, 465, 499, 596, 535, 628, 632; 128/641, 639

[56] References Cited

U.S. PATENT DOCUMENTS

| | | | |
|---|---|---|---|
| 3,631,851 | 1/1972 | Hesen | 128/2.06 R |
| 3,812,845 | 5/1974 | Partridge | 128/2.06 R |
| 4,215,236 | 7/1980 | Reiser | 174/59 |
| 4,267,576 | 5/1981 | Power et al. | 364/578 |
| 4,351,343 | 9/1982 | Parrillo et al. | 128/695 |
| 4,352,163 | 9/1982 | Schultz, Jr. et al. | 364/801 |
| 4,658,422 | 4/1987 | Sparks | 439/142 |
| 4,695,258 | 9/1987 | Hanson et al. | 439/329 |
| 4,710,137 | 12/1987 | Perdue et al. | 439/465 |

*Primary Examiner*—P. Austin Bradley
*Attorney, Agent, or Firm*—Anthony G. Eggink

[57] ABSTRACT

The electrode belt adapter assembly is for communicatively connecting the terminal end of a flexible electrode belt device to the cable end of an EGG apparatus having a plurality of leads at its terminal end. The electrode belt adapter assembly is comprised of a lightweight housing assembly having a lockable cover structure to provide access thereinto and having a first aperture and a set of second apertures to respectively provide communicative access of the electrode belt terminal end and the leads of the cable set end. A circuit board assembly having a plurality of connectors is integrally mounted within the housing assembly. An electrode belt connector assembly is mounted on the circuit board and is aligned with the first aperture. The circuit board assembly further has a connection network with a plurality of leads and post connectors at predetermined locations in electrical communication with the electrode belt connector assembly.

20 Claims, 4 Drawing Sheets

ELECTRODE BELT ADAPTER

BACKGROUND OF THE INVENTION

This invention relates to an adapter assembly to facilitate the connection between a flexible and layered electrical device and the cable assembly of an electrical apparatus. Particularly, this invention relates to an electrode belt adapter assembly to facilitate the connection of a flexible electrode belt to the cable assemblies extending from electrocardiograph (ECG) machines.

Testing and analysis apparatus, such as ECG machines, have cable sets or assemblies which permit various signals to be transmitted from external sources, such as patient electrodes. At the apparatus, the cable set is typically inserted into a circular type connector. At the opposite ends of the cable set, typically alligator clips or snap-type ends are used for connection to electrode leads, for example. The connector end of any particular cable set, however, may vary in configuration and operation depending upon the manufacturer of the testing apparatus. Therefore, for the connection of a new device to a known apparatus, its connection requires a specific connector configuration designed for that particular apparatus, or an adapter assembly for connection to the opposite ends of the existing cable set.

The adapter assembly of this invention provides a connection to a cable set for use with flat and flexible electrical devices, such as electrode belts, with various cable assemblies extending from testing and analysis apparatus, such as ECG machines.

As discussed, cable sets or assemblies are secured at one end to the testing apparatus typically by means of a circular connector plug. At their opposite ends, typically alligator clips or, more commonly, snap connectors are utilized. The snap connectors at the terminal ends of the wires of the cable assembly are comprised of female type lead ends which are designed for mating connection to male rivets or post structures located at the ends of the patient electrode leads, for example.

The advent of flexible and flat conductive membrane structures in the electronic industry has presented unique problems relating to the electrical connection of these flat structures to the various cable assemblies extending from the testing and analyzing apparatus, with which they are designed to be used. As a particular example, the flexible electrode belt devices of U.S. patent application Ser. No. 807,346, now abandoned filed Dec. 10, 1985, discloses a flexible and layered electrode belt structure used, for example, with standard ECG units. The adapter assembly of this invention is constructed and arranged to provide the convenient means for connecting these flexible membrane or layered conductive structures to cable sets of electrical apparatus.

An additional problem presented by the use of the flexible and flat membrane structures is the assurance that the various conductive leads are properly connected to the respective terminal wires of the cable set assembly. The adapter assembly of this invention is further constructed and arranged to provide quick and accurate means for connecting these flexible conductive structures to the proper terminal wires of the cable set assembly.

The prior art discloses various adapter devices to facilitate the interconnection of cable sets to particular cooperating structures. For example, various junction blocks, junction boxes and housing assemblies are disclosed to provide connection means relating to cable assemblies. However, these housing and junction box structures provide interconnection means for specific cable or lead requirements. And, none so far as is known, provides interconnection means to permit the quick, economical and convenient connection of a flexible electrode belt, for example, to the cable leads of an ECG unit. The electrode belt adapter according to the teachings of this invention provides such an adapter assembly.

SUMMARY OF THE INVENTION

The electrode belt adapter is for communicatively connecting the terminal end of a flexible electrode belt device to the plurality of leads extending from a cable assembly of an electrical diagnostic apparatus, such as an ECG unit. The electrode belt adapter is comprised of a housing assembly having ingress means to cover and provide access thereinto and further having first and second aperture means to provide communicative access thereinto of the electrode belt terminal end and the leads of the cable end.

A circuit board assembly having a plurality of connector means is provided within the housing assembly. An electrode belt connector assembly is mounted on one end of the circuit board and in alignment with the first aperture means in the housing assembly structure.

The connector means extend upwardly from the circuit board and are further arranged thereon in a predetermined manner to provide for quick and reliable cable assembly lead connection. The connector means are accessible to the cable assembly leads through the second aperture means. The circuit board assembly further has a connection network with a plurality of leads to communicate the electrode belt connector assembly to the plurality of connector means.

Also provided is an electrode belt adapter wherein the electrode belt adapter has current limiting circuits in the circuit board and which are operative on each of the leads of the connection network.

Further provided is an electrode belt adapter wherein the connector means are comprised of snap assemblies for mating connection to the snap leads of a cable end and wherein the adapter assembly has connecting means for alligator type clips.

Also provided is an electrode belt adapter assembly wherein the connector assembly is placed over the conductive contacts of the circuit board, the conductive contacts being the terminating ends of the electrical connection network of the circuit board.

Also provided are electrode belt adapter assemblies wherein the housing assembly has a generally rectangular body structure having a hinged cover, wherein the first and second aperture means are disposed in opposite end walls of the rectangular body structure, wherein the electrode belt connector assembly and the plurality of connector means are respectively mounted adjacent the first and second aperture means, and wherein the ingress means is transparent.

Further provided by this invention is an electrode belt adapter assembly wherein ten snap assemblies are provided in a predetermined arrangement on the circuit board, and wherein the ingress means is an insulator and is adapted to secure the cable end leads in a manner to provide strain relief to the cable end leads of the cable set.

And, provided by this invention are identifying means for the connector means of the circuit board to insure quick and accurate cable assembly connection.

These and other benefits of this invention will become clear from the following description by reference to the drawing figures.

DESCRIPTION OF THE PREFERRED EMBODIMENTS

Figure 1:
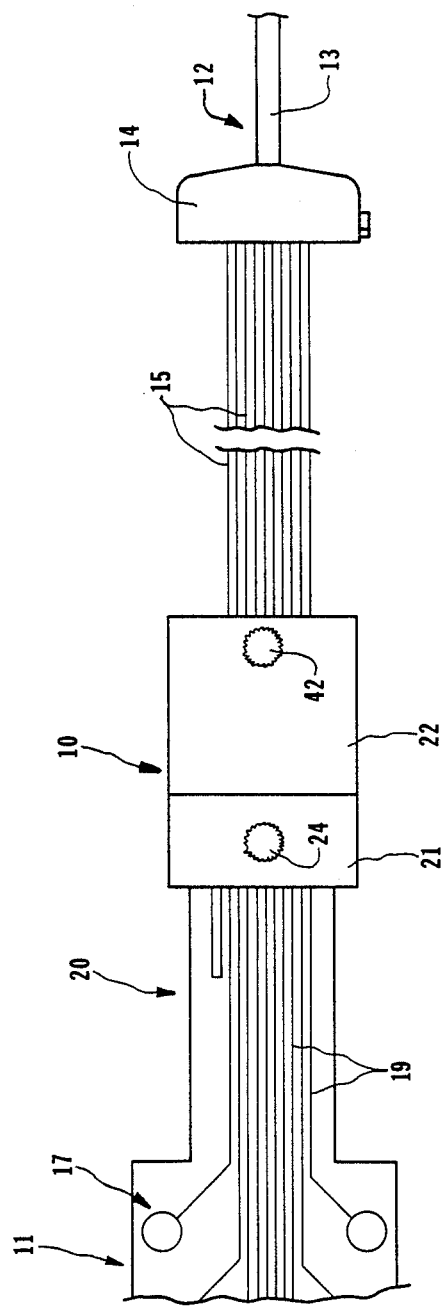
FIG. 1 is a top plan view showing the electrode belt adapter of this invention in use and connecting a flexible conductive electrode belt device with the cable set extending from an apparatus.

Referring to FIG. 1, the electrode belt adapter 10 of this invention is shown connecting an electrode belt device 11 to an ECG cable set 12. The ECG cable set 12 is a typical cable assembly extending from a testing or analyzing apparatus, such as an ECG unit. The ECG cable set 12 typically has a cable 13 connected to a terminal junction 14 from which a specified number of lead wires 15 extend. On the ends of the lead wires 15 are connectors, such as of the alligator clip or snap-on type, as further shown in FIG. 3.

Figure 2:
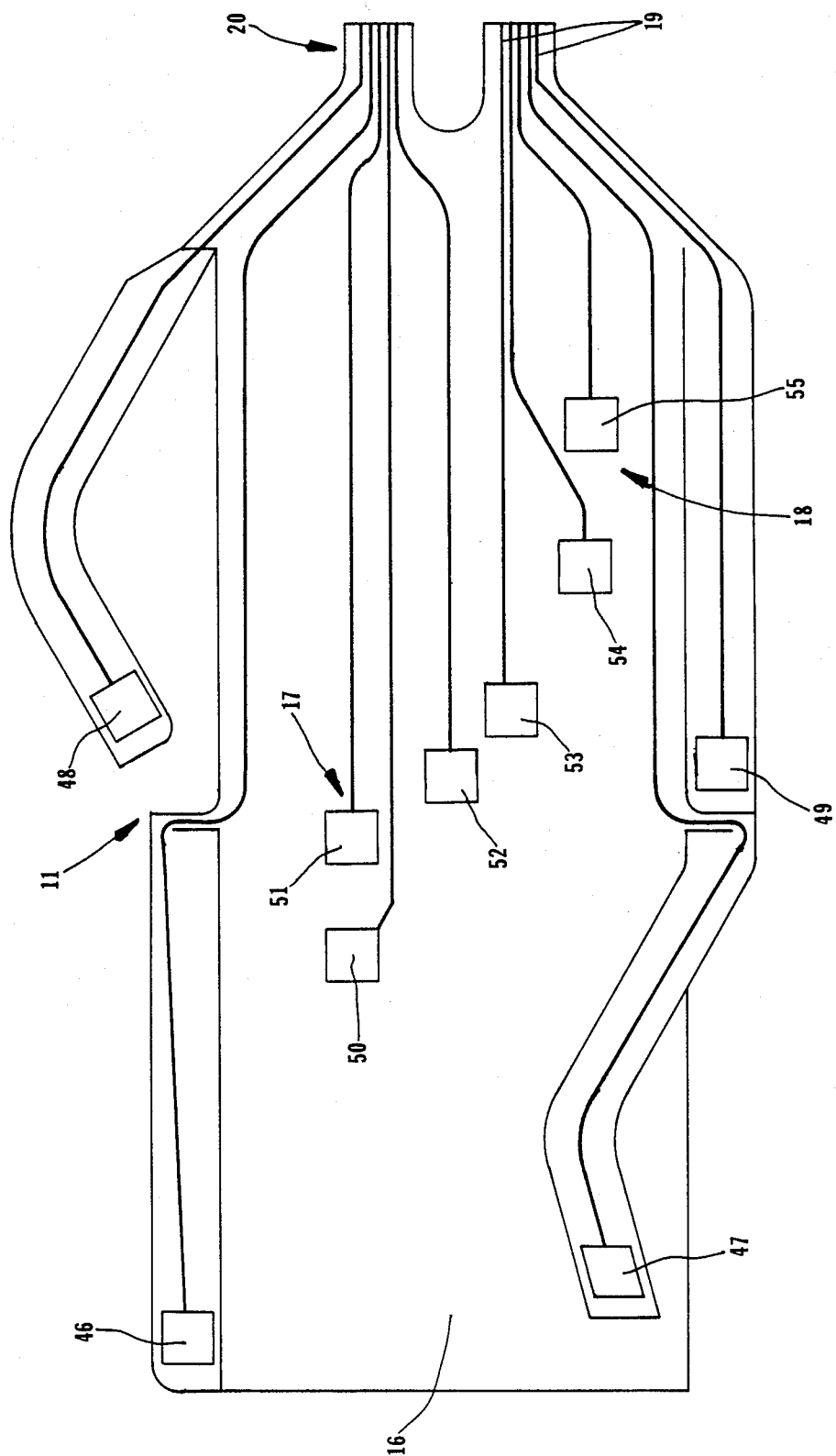
FIG. 2 is a top plan view showing a particular flexible conductive electrode belt device for connection to the electrode belt adapter of this invention.

The electrode belt device 11 shown in FIG. 2 is the subject of pending U.S. patent application Ser. No. 807,346 filed on Dec. 10, 1985, now abandoned, and which discloses a flexible and layered structure having an electrode belt body structure 16 with patient electrodes 17 and 18. The electrode belt device 11 has a terminal end 20 which exposes a plurality of electrode leads 19 in electrical connection with the patient electrodes 17 and 18 and which is shown connected to the electrode belt adapter 10.

Electrode belt devices 11 are manufactured in a variety of configurations wherein the patient electrodes 17 are placed in predetermined locations on the body of a patient for the purpose of detecting and transmitting bioelectrical signals. For purposes of this electrode belt adapter invention it is important to note that the electrode leads 19 at the terminal end 20 of the belt device 11 correspond to patient electrodes 17, which are placed at predetermined areas of the human body.

The specific electrode belt 11 structure shown in FIG. 2 is designed for use with ECG units. The electrode belt body structure 16 has electrode portions that are movable with respect to the main portion of the device. Electrode 46 is movable for placement on the patient's body commonly referred to as the right arm (RA) location. Similarly, electrode 48 is placed at the left arm (LA) location and the electrodes 47 and 49 are respectively placed on the right leg (RL) and left leg (LL) locations. The remaining electrodes 50-55 are for the V1-V6 locations.

Figure 3:
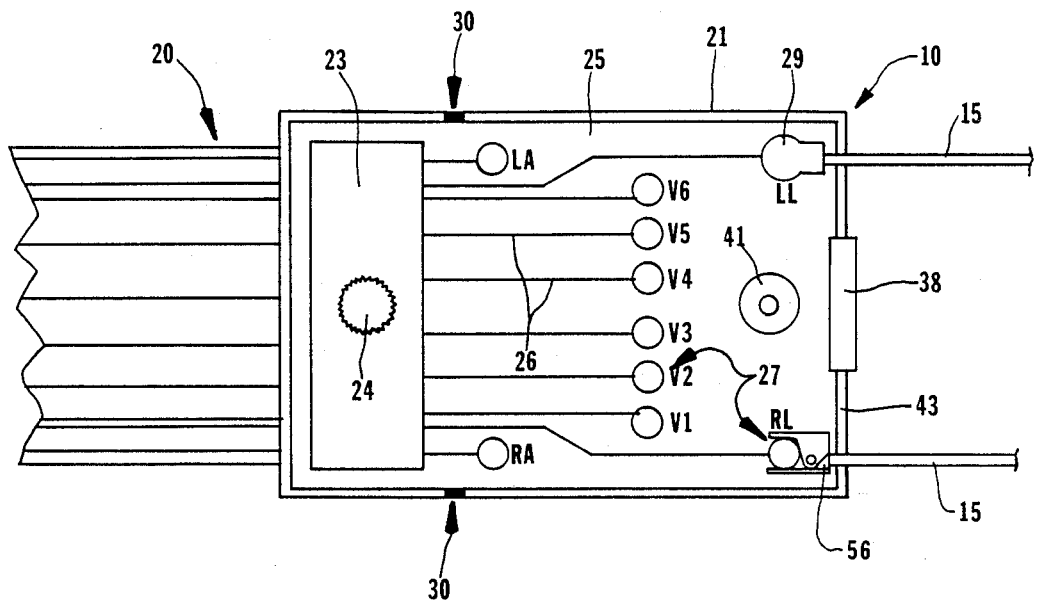
FIG. 3 is a top schematic view showing the interior of the housing assembly of the electrode belt adapter.
Figure 4:
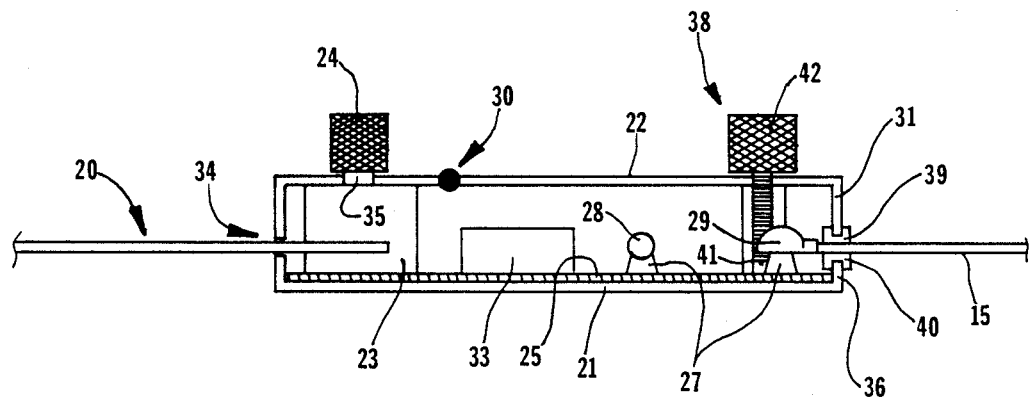
FIG. 4 is a lateral sectional view showing the interconnection of the elements in the housing assembly of the electrode belt adapter.

FIGS. 3 and 4 show the electrode belt adapter 10 as having a body or housing structure 21 and a top cover 22 which is hinged to the housing 21 by hinge means 30. The housing structure 21 is preferably of a lightweight construction, such as a molded plastic, because the adapter assembly 10 is generally used in an unsupported state between the terminal end 20 of the electrode belt 10 and the lead wires 15 of the erminal junction 14. Additionally, the interior surfaces of the housing structure can be coated of a conductive materials for shielding purposes so as to minimize electrical interference.

Inside the belt adapter body structure 21, a circuit board 25 is shown mounted onto the bottom surface or is integral with the housing structure 21. The circuit board 25 has mounted thereon a belt connector assembly 23 having a belt securement knob 24 which is accessible to the outside of the housing 21. The belt connector assembly 23, as further disclosed in pending U.S. patent application Ser. No. 939,715, filed on Dec. 9, 1986, now U.S. Pat. No. 4,695,258, constructed and arranged to receive the terminal end 20 of electrode belt device 11.

In electrical communication with the belt connector assembly 23 are a number of circuit leads 26 disposed in the circuit board 25. At one end and in electrical communication with circuitry network 26 are connector posts 27. The connector posts 27 are constructed and arranged to receive the snap connectors 29 fixed at the ends of lead wires 15. Alternatively, as shown in FIG. 3, a lead wire 15 having an alligator type clip 56 can be releasably fixed to the connector posts 27.

As is particularly shown in FIG. 3, the connector posts 27 are connected and spacially arranged on the circuit board 25 in a predetermined configuration. As shown, each connector post 27 has an adjacent marking on the circuit board for use by the operator during connection. The markings shown relate to the corresponding placement of the electrode belt's individual electrodes. This particular connector post 27 arrangement represents and provides for the quick and accurate connection of an electrode belt device 11 for use with a standard 12 lead ECG cable set.

In that arrangement, as shown with respect to the end wall 43 of housing 21, the bottom end post positions 27 cooperate with the belt connector assembly 23 and the terminal end leads 19 to designate the Right Leg (RL) and Left Leg (LL) connectors for receiving the snap connectors 29 of the corresponding lead wires 15. The outward end post positions are designated for RA and LA connection, while the central row of posts 27 are designated for V1-V6 connection. Preferably, these patient location corresponding designations are printed on the circuit board 25 next to the appropriate post 27 to further ensure that the proper lead wire 15 connections are made. Although the visual markings here shown are for an electrode belt structure designed for use with ECG units, other visual markings and post 27 placements can accordingly be made for other belt structures, as for use on other human body locations.

As further shown in FIG. 4, the belt adapter body structure 21 has an elongated slot or aperture 34 through which the terminal end 20 of electrode belt device 11 is placed. Adjacent the elongated slot 34 and inside the belt adapter housing structure 21 is belt connector assembly 23 which is communicatively mounted to circuit board 25 above the terminating circuit board contacts and which has its belt securement knob accessible for use on the outside of the belt adapter housing 21. As shown, the securement knob 24 extends through aperture 35 in the top wall of the adapter housing 21. For purposes of the specific configuration of the adapter housing structure 21 it is important that means are provided for the insertion of a terminal end 20 as well as access means to activate the connector assembly 23.

The electrode belt adapter 10 further has a top cover 22 incorporated in its body structure 21. The top cover 22, preferably constructed of a transparent, insulative material, is connected at hinge means 30 so the circuit board 25 and particularly the connector posts 27 are exposed for view and use. This is important as discussed above because the connector posts 27 are arranged on circuit board 25 so that electrode leads 19 of electrode belt device 11 are in a predetermined manner electrically connectable via belt connector assembly 23 to the connector posts 27 to permit the standard lead wires 15 of an ECG cable set, for example, to be visually matched by means of connecting their respective snap connectors 29 to those particular connector posts 27.

Figure 5:
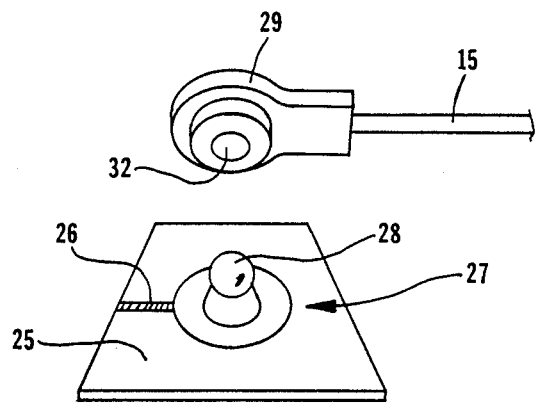
FIG. 5 is a perspective view showing a connector assembly mounted to the circuit board of the electrode belt adapter.

FIG. 5 further illustrates a connector post 27 and snap connector 29. This particular connection means is commonly used in the ECG cable set 12 of ECG units. They provide a quick and secure means for connecting these ECG cable sets 12. As shown, the connector post 27 is mounted to the circuit board 25 and electrically connected by lead circuitry 26. The connector cavity 32 of snap connector 29 is placed over head 28 to securely fasten or connect the lead wires 15 to the electrode belt adapter 10.

Further shown in FIG. 4 is a current limiter circuit 33 mounted on the circuit board 25. This current limiter circuit 33 is disclosed in pending U.S. patent application Ser. No. 915,778, filed on Oct. 6, 1986 now U.S. Pat. No. 4,744,369. The current limiter circuit 33 disclosed is for providing current limiter protection between an electrode belt 11 and an ECG unit, for example. Thus, a current limiter circuit 33 can conveniently be mounted to or be part of the circuit board 25 for each circuit lead 26 so as to effectively protect its connection.

Figure 6:
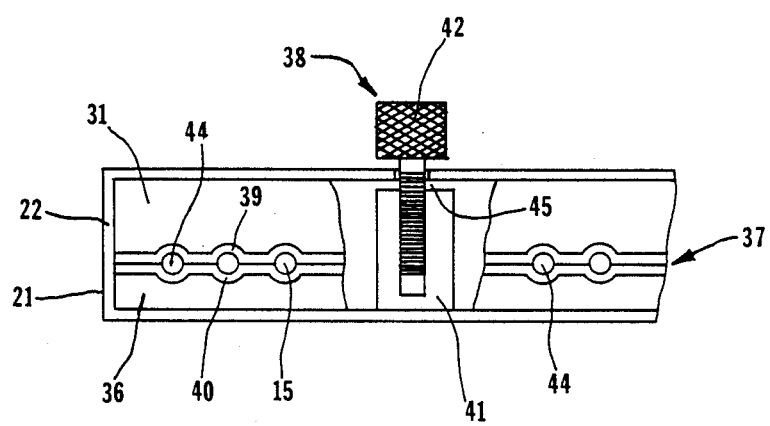
FIG. 6 is a frontal view of the housing assembly and showing the leads of a cable set connecting thereto.

Referring to FIGS. 4 and 6, the top cover 22 on adapter housing 21 is provided wih a downward edge 31 which cooperates with the upward wall 36 to close the housing. The interface between the cover edge 22 and the upward wall 36 define a number of apertures 44 for entry of the lead wires 15. Also provided are resilient upper and lower pad members, 39 and 40 respectively secured to the ends of the cover edge 31 and upward wall 36 for providing strain relief to the lead wires 15.

The top cover 22 additionally has cover securement or locking means 38 to secure it to the remaining housing structure 21 in a closed position. An internally threaded post 41, for example, is shown attached or integral with the bottom of the housing 21. Through an aligned aperture 45 in the top cover 22, a threaded knob structure 42 is provided for threading into the post 41 to secure and lock the lead wires 15 in place.

As discussed in the above mentioned disclosure for the belt connector assembly 23, several embodiments are shown. Each of these structural configurations can be utilized in the electrode belt adapter 10. The belt connector assembly 23 is mounted to the circuit board 25 and its second aperture is exposed for receiving the terminal end 20 of an electrode belt device 11. Additionally, the means to releasably urge the terminal contact end of the electrode belt device 11 to the circuit board 25 is also exposed for use outside the belt adapter body structure 21 of electrode belt adapter 10.

As many changes are possible to the embodiments of this invention, utilizing the teaching thereof, the descriptions above and the accompanying drawings should be interpreted in the illustrative and not in the limited sense.

That which is claimed is:

1. An adapter assembly to facilitate the electrical connection of the terminal end of a flexible conductive device to the leads of a cable assembly of an electrical diagnostic apparatus, said adapter assembly comprising:
    (a) a lightweight housing assembly having an openable and lockable cover structure defining a plurality of apertures at one end and an elongated aperture at its opposite end,
    (b) a circuit board assembly fixed within said housing structure and having a conduction network with a plurality of leads and having at one end a plurality of terminating connector means extending upwardly therefrom, said terminating connector means further being constructed and arranged on said circuit board in a predetermined configuration and being accessible through said cover of said housing structure, and
    (c) a connector assembly mounted on the opposite end of said circuit board in communication with said conduction network and being aligned with said elongated aperture means of said housing assembly, whereby the connection of the terminal end of the flexible conductive device through said elongated aperture and into said connector assembly permits a user to quickly and accurately provide communication with the electrical apparatus by means of the connection of the cable assembly leads to the terminating connector means through the plurality of apertures defined by said housing assembly cover structure.

2. The adapter assembly of claim 1, wherein a set of ten terminating connector means are provided extending from said circuit board, said set of connector means being arranged in a configuration visually determinable and being marked to the corresponding body electrode placement on a patient for use with ECG cable sets.

3. The adapter assembly of claim 1, wherein said circuit board additionally has a current limiting circuit connected to each said conduction network lead.

4. The adapter assembly of claim 1, wherein said upwardly extending connector means are comprised of a snap-type assembly for mating connection to the snap lead of a cable end.

5. The adapter assembly of claim 1, wherein said connector assembly is constructed and arranged to receive an electrode belt device.

6. The adapter assembly of claim 1, wherein said said housing assembly is a rectangular body structure having an end wall portion and wherein said cover structure is of a transparent material having a downwardly extending lip portion for engaging said end wall portion, said end wall portion and said lip portion further defining said plurality of apertures for receiving the leads of a cable assembly.

7. The adapter assembly of claim 6, wherein upper and lower resilient pad structures are fixed to said wall portion and said lip portion to provide strain relief to the cable assembly leads.

8. The adapter assembly of claim 1, wherein each said connector of said predetermined connector means configuration is visually marked for accurate connection with the cable assembly.

9. The adapter assembly of claim 8, wherein said visual markings correspond to the electrode placement for ECG purposes.

10. An electrode belt adapter for communicatively connecting the terminal end of a flexible electrode belt device to the plurality of leads extending from a cable end of an electrical apparatus, said electrode belt adapter comprising:
(a) a lightweight housing assembly having ingress means to cover and provide access thereinto, said housing assembly further having first and second aperture means to provide communicative access of theelectrode belt terminal end and the leads of the cable end thereinto, said housing assembly further having hand-operable cover locking means,
(b) a circuit board assembly having a plurality of connector means mounted thereon and being integral with said housing assembly and further being aligned with said second aperture means, said connector means being connectible to the cable end of the electrical apparatus, said circuit board assembly further having a conductive connection network having a plurality of leads in communication with said plurality of connector means, and
(c) an electrode belt connector assembly mounted to said circuit board within said housing assembly and being aligned with said first aperture means.

11. The electrode belt adapter of claim 10, wherein said electrode belt adapter additionally has a current limiting circuit in said circuit board operative on each said lead of said conductive connection network.

12. The electrode belt adapter of claim 10, wherein said connector means are comprised of post structures to receive an alligator clip connector.

13. The electrode belt adapter of claim 10, wherein said electrode belt connector assembly is comprised of an alignment body structure having a central aperture in alignment with the terminating circuit board contacts of the circuit board, a horizontal insertion aperture for the electrode belt terminal end, an elastomeric conductor and clamping means to urge the electrode belt terminal end into contact with the elastomeric conductor and the terminating circuit board contacts.

14. The electrode belt adapter of claim 10, wherein said ingress means is transparent.

15. The electrode belt adapter of claim 10, wherein said ingress means is an insulator and adapted to secure the cable end leads to said connector means on said circuit board and to provide strain relief to the cable end leads, 16. The electrode belt adapter of claim 10, wherein said connector means are comprised of snap assemblies for mating connection to the snap leads of a cable end.

17. The electrode belt adapter of claim 16, wherein ten snap assemblies are provided in a predetermined arrangement on said circuit board in said housing assembly for use with ECG cable sets.

18. The electrode belt adapter of claim 10, wherein said housing assembly has a generally rectangular body structure having a hinged cover.

19. The electrode belt adapter of claim 18, wherein said first and second aperture means are disposed in opposite end walls of said rectangular body structure.

20. The electrode belt adapter of claim 19, wherein said electrode belt connector assembly and said plurality of connector means are respectively mounted adjacent said first and second aperture means.

* * * * *